United States Patent
Valaie

(10) Patent No.: US 7,682,337 B2
(45) Date of Patent: Mar. 23, 2010

(54) METHOD AND APPARATUS FOR GAINING PERCUTANEOUS ACCESS TO A BODY

(75) Inventor: Arman H. Valaie, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 12/022,331

(22) Filed: Jan. 30, 2008

(65) Prior Publication Data

US 2008/0188812 A1    Aug. 7, 2008

Related U.S. Application Data

(60) Provisional application No. 60/899,996, filed on Feb. 7, 2007.

(51) Int. Cl.
*A61M 5/178* (2006.01)

(52) U.S. Cl. ............................. 604/164.01; 604/164.13

(58) Field of Classification Search ............. 604/164.01
See application file for complete search history.

(56) References Cited

U.S. PATENT DOCUMENTS

| | | | | |
|---|---|---|---|---|
| 4,404,159 A | 9/1983 | McFarlane | ................... | 264/296 |
| 4,405,314 A | 9/1983 | Cope | ........................... | 604/51 |
| 4,629,450 A | 12/1986 | Suzuki et al. | ................ | 604/164 |
| 4,650,472 A | 3/1987 | Bates | .......................... | 604/158 |
| 5,489,269 A | 2/1996 | Aldrich et al. | ................. | 604/95 |
| 5,573,520 A | 11/1996 | Schwartz et al. | ............. | 604/282 |
| 5,702,373 A | 12/1997 | Samson | ....................... | 604/282 |
| 6,053,904 A | 4/2000 | Scribner et al. | .............. | 604/527 |
| 6,610,046 B1 * | 8/2003 | Usami et al. | ................. | 604/530 |
| 2004/0030319 A1 * | 2/2004 | Korkor et al. | ................ | 604/506 |
| 2005/0004523 A1 * | 1/2005 | Osborne et al. | ......... | 604/164.01 |
| 2006/0052750 A1 * | 3/2006 | Lenker et al. | ........... | 604/164.01 |
| 2006/0270988 A1 | 11/2006 | Valaie | ......................... | 604/158 |
| 2007/0060927 A1 * | 3/2007 | Longson et al. | .............. | 606/108 |

FOREIGN PATENT DOCUMENTS

| | | |
|---|---|---|
| EP | 0 778 045 A2 | 6/1997 |
| EP | 0 808 637 A3 | 3/1998 |
| EP | 1 092 449 A1 | 4/2000 |
| WO | WO 93/02735 A1 | 2/1993 |
| WO | WO 2005/00467 A2 | 1/2005 |

OTHER PUBLICATIONS

Neff Percutaneous Access Sets, Cook Diagnostic & Interventional Products Catalog, 2003, p. 54.

\* cited by examiner

*Primary Examiner*—Nicholas D Lucchesi
*Assistant Examiner*—Jason Flick
(74) *Attorney, Agent, or Firm*—Brinks Hofer Gilson & Lione

(57) ABSTRACT

The present invention is directed to apparatus and methods for gaining percutaneous access to body anatomy, for example an organ or a body lumen. According to one aspect of the invention, an apparatus is provided comprising a needle and an outer sheath. The needle is receivable within the outer sheath and comprises a plurality of outer diameters. A distal portion of the needle has a lesser diameter than a proximal portion of the needle. Other embodiments are also disclosed.

21 Claims, 3 Drawing Sheets

METHOD AND APPARATUS FOR GAINING PERCUTANEOUS ACCESS TO A BODY

RELATED APPLICATION

The present patent document claims the benefit of the filing date under 35 U.S.C. §119(e) of Provisional U.S. Patent Application Ser. No. 60/899,996, filed Feb. 7, 2007, which is hereby incorporated by reference.

BACKGROUND

1. Technical Field

The present invention is directed to apparatus and methods for gaining percutaneous access to body anatomy, for example an organ or a body lumen.

2. Background of the Invention

Many medical procedures require the percutaneous placement of an interventional medical device, such as a catheter, into a body lumen such as an artery or vein. Such interventional devices may be used for, among other things, blood pressure monitoring, blood sampling, and the administration of fluids and medicaments to a patient.

Typically, such devices are introduced into the vascular system using the well-known Seldinger percutaneous entry technique. In the Seldinger technique, the physician makes an entry into the artery or vein with a beveled needle. A wire guide is passed through the bore of the needle into the artery or vein. The needle is thereafter withdrawn, leaving the wire guide in place. The catheter or other interventional device is then passed over the wire guide, through the puncture, and into the artery or vein at the needle puncture site. Once the catheter is in place, the wire guide can be withdrawn.

One of the disadvantages of this procedure is that the initial needle stick must normally be made with a needle that is large enough to accept the wire guide. Conventional wire guides often comprise a tightly wound helical stainless steel wire coil. In order to have sufficient rigidity to properly support and lead many standard catheters and other interventional devices in common use in modern medicine, such wire guides are typically constructed to have an outer diameter in a range on the order of 0.035 to 0.038 inch (0.89 or 0.97 mm). This diameter of wire guide will typically pass through an 18 gauge thin wall needle. An 18 gauge needle typically has a 0.050 inch (1.27 mm) outer diameter (O.D.) and a 0.042 inch (1.07 mm) inner diameter (I.D.).

The 18 gauge needle is the most common sized needle used for initial vascular access, and has become a standard needle for use with the Seldinger technique for percutaneous catheterization. However, the O.D. of an 18 gauge needle is just large enough to damage tissue or cause excessive bleeding if it does not enter the vessel correctly, or if it inadvertently penetrates an organ or other unintended body structure. As a result, it is desirable to utilize a smaller gauge needle, such as a 21 gauge thin wall needle, for initial entry. A 21 gauge thin wall needle typically has a 0.032 inch (0.81 mm) O.D. and a 0.022 inch (0.56 mm) I.D., or smaller. Needles of 21 gauge thin wall, or smaller, are considered small enough that they do not damage tissue or organs, or cause excessive bleeding if inserted off target. In addition, smaller gauge needles generally have correspondingly shorter bevels at the needle tip compared to the size of the bevel tip of an 18 gauge needle. Thus, it is much easier to get a short bevel into the lumen of a small vessel than the longer bevel of the 18 gauge needle.

Unfortunately, the bore of a needle of 21 gauge, or smaller, is not large enough to enable a standard 0.035 inch or 0.038 inch (0.89 mm or 0.97 mm) diameter wire guide to be passed therethrough. The largest wire guide that can be easily introduced into such small gauge needles is normally a wire of 0.018 inch (0.46 mm) O.D. However, many diagnostic and interventional devices need at least a 0.035 inch (0.89 mm), and more preferably a 0.038 inch (0.97 mm), diameter wire guide to provide sufficient support to enable the physician to optimally introduce and manipulate the device through the vasculature over the wire. Thus, unless a larger diameter wire guide is introduced into the vasculature, many such devices cannot be successfully introduced.

U.S. Pat. No. 4,650,472 describes an apparatus which enables a physician to introduce a medical device, such as a catheter, into the body of a patient by making the initial puncture with a small gauge needle, such as a 22 gauge (0.028 inch; 0.72 mm O.D.) needle, in place of the larger conventional 18 gauge needle. The '472 patent is incorporated by reference herein. A 0.018 inch (0.46 mm) outer diameter wire guide is initially inserted through the bore of the small gauge (e. g. 22 gauge) needle. The needle is thereafter withdrawn, and a removable inner cannula, or dilator, is provided over the wire guide but inside an outer sleeve portion of the catheterization apparatus. This removable inner cannula has a tapered tip, and provides a transition between the large distal opening of the outer sleeve and the 0.018 inch wire guide. The inner cannula is generally on the order of 0.038 inch (0.97 mm) O.D., and the outer sleeve is sized to fit over the inner cannula.

The outer sleeve and the inner cannula of the apparatus disclosed in the '472 patent are normally inserted into the blood vessel in tandem. The diametrical transition of the leading end of this tandem is intended to minimize the trauma that may otherwise be caused by the insertion of a large diameter outer sleeve over a small diameter wire guide. Once the outer sleeve is properly positioned within the blood vessel, the inner cannula and the smaller wire guide can be withdrawn, leaving the outer sleeve in place. A larger diameter (0.035 to 0.038 inch) (0.89 to 0.97 mm) wire guide can then be introduced through the outer sleeve and into the vessel.

In summary, the '472 patent device is used according to the following steps:

1. Initial needle stick with a 22 gauge needle.
2. Insert a 0.018 inch diameter wire guide through needle.
3. Remove the needle leaving the 0.018 inch diameter wire guide in place.
4. Insert the outer sleeve and the inner cannula in tandem.
5. Remove the inner cannula and 0.018 inch diameter wire guide leaving the outer sleeve in place.
6. Insert a larger 0.035-0.038 inch diameter wire guide through the outer sleeve.

If desired, the outer sleeve can thereafter be removed from the patient, leaving the larger wire guide in the vessel ready to accept a catheter or other interventional device. The apparatus of the '472 patent has been successfully used to percutaneously insert a medical device, such as a catheter, having a large diameter O.D. into a blood vessel when the initial insertion is made with an introducer needle and a wire guide which are much smaller in diameter than the distal opening of the catheter.

Other medical devices are used for percutaneous access to organs or other anatomy within a body for procedures such as interventional radiology One such device is the "Neff Percutaneous Access Set" available from Cook Incorporated, catalogue number prefix NPAS. The set has an access needle, a wire guide, a stiffening cannula, an introducer (functionally a dilator), and a sheath (functionally a catheter or outer sleeve). The first step in using the set is to penetrate the skin and body with the access needle and place the tip of the access needle at a desired location. The wire guide is then inserted through the access needle. Next, the access needle is removed leaving the wire guide in place. The introducer is inserted into the sheath and the stiffening cannula is inserted into the introducer. The assembly is then inserted into the body over the wire guide. Finally, the wire guide, introducer and stiffening cannula are removed, leaving the sheath in place.

In summary, the Neff device is used according to the following steps:

1. Initial needle stick and placement of the access needle.
2. Insert the wire guide through the access needle.
3. Remove the access needle leaving the wire guide in place.
4. Insert the sheath/introducer/stiffening cannula assembly over the wire guide.
5. Remove the introducer/stiffening cannula leaving the sheath in place.

Apparatus and methods for gaining percutaneous access to body anatomy having fewer components and fewer steps are generally desired.

BRIEF SUMMARY

According to various aspects of the invention, apparatus and methods for gaining percutaneous access to anatomy within a body are provided. The apparatus comprises a needle having an intermediate taper, and an outer sleeve that receives the needle with a taper disposed proximal of the needle. The needle has a needle lumen that receives a wire guide.

DETAILED DESCRIPTION OF THE DRAWINGS AND THE PRESENTLY PREFERRED EMBODIMENTS

Figure 1:
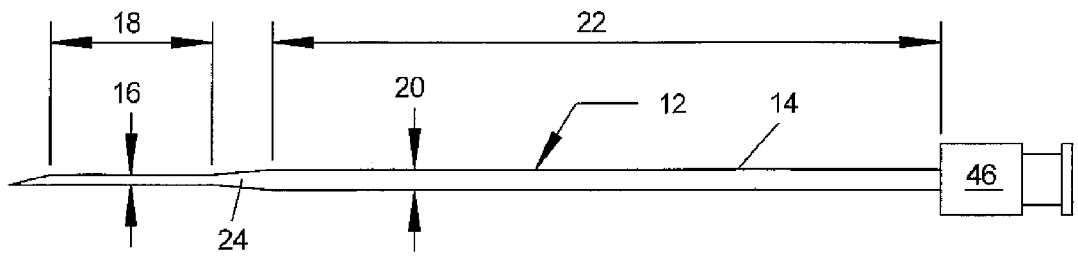
FIG. 1 presents a side view of a needle according to an aspect of the invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the term "proximal" is used in its conventional sense to refer to the end of the apparatus or structure that is closer to the operator. The term "distal" is used in its conventional sense to refer to the end of the apparatus or structure that is further from the operator.

Figure 2:
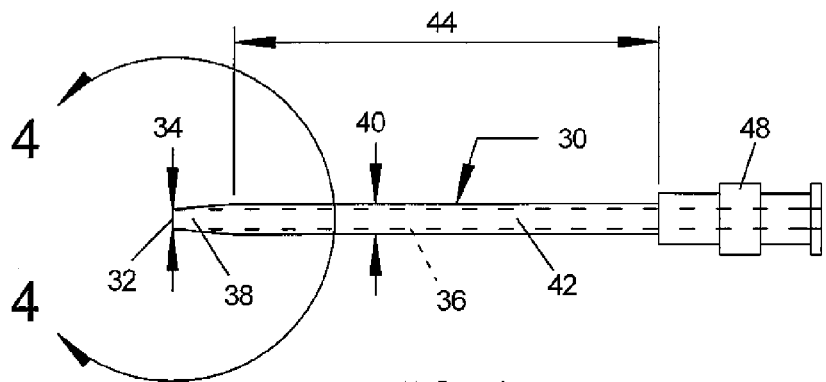
FIG. 2 presents a side view of an outer sheath according to an aspect of the invention.
Figure 3:
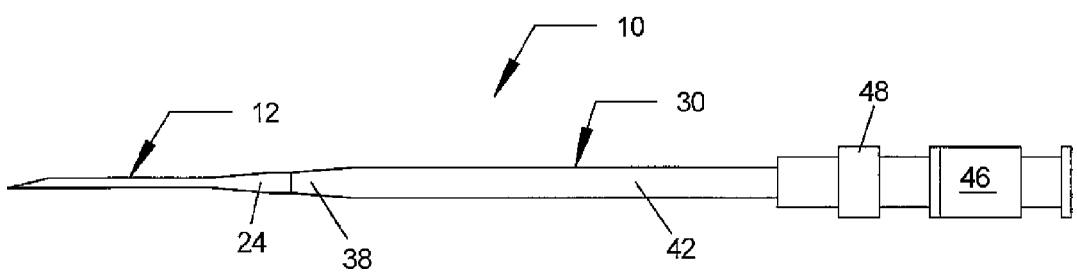
FIG. 3 presents an introducer apparatus according to an aspect of the invention wherein the needle of FIG. 1 is received within the outer sheath of FIG. 2.

Referring now to FIGS. 1 through 3, an apparatus 10 for gaining percutaneous access to a body lumen, for example a blood vessel, is presented according to one aspect of the invention. The apparatus 10 comprises a needle 12 defining an outer surface 14 having a first outer diameter 16 along a distal first length 18. The needle 12 also defines a second outer diameter 20 along a proximal second length 22, as well as a first taper 24 contiguous with the first outer diameter 16 and the second outer diameter 20. The first taper 24 is intermediate the first length 18 and the second length 22. The second outer diameter 20 is greater than the first outer diameter 16. The needle 12 may have a needle lumen that extends longitudinally through it. Apparatus 10 also comprises an outer sleeve 30 terminating at a distal end 32 having a third outer diameter 34 and an outer sleeve lumen 36 extending longitudinally therethrough. The outer sleeve comprises a second taper 38 from the third outer diameter 34 at the distal end 32 to a fourth outer diameter 40 greater than the third outer diameter 34 and proximal thereto, and a shaft portion 42 having the fourth outer diameter 40 along a shaft length 44 contiguous with the second taper 38.

As shown in FIG. 3, the needle 12 is receivable within the outer sleeve lumen 36 with the second taper 38 disposed proximal of the first taper 24. The needle 12 and outer sleeve 30 may have hubs 46 and 48, respectively that are of conventional construction. The hub configurations shown in the figures merely represent examples of suitable hubs. One or both may have a Luer connector. The specific design of the hubs is not germane to an understanding of the present invention, and therefore, no further description is provided.

The hubs 46 and 48 may act as a positioning structure that releasably fixes the needle 12 to the outer sleeve 30. For example, hub 46 may comprise male threads that are received within complementary female threads within hub 46, and the two may be engaged and disengaged by relative twisting. Other arrangements are contemplated within the practice of the invention such as press fits and snap fits, or other suitable structure that releasably fixes the needle 12 to the outer sleeve 30 The hubs 46 and 48 may be formed from a metal, such as stainless steel, or a medical grade polymeric material, similar to current material used in Needle hubs and Dilators Hubs. Hubs 18, 38 may be of any conventional design that permits releasable engagement therebetween.

The outer sleeve 30 may be formed, for example, from medical grade polyethylene similar to materials presently used in dilators, with the tip formed by operators trained in the art of forming tapers on medical devices, for example by inserting a tip lubricated with silicone into a heated glass mold. The apparatus 10 can be of any conventional size for its intended purposes. Preferably, the outer sleeve 30 does not exceed about 6 French in diameter, and more preferably, does not exceed about 5 French. The inner lumen 32 of the outer sleeve preferably has a diameter of about 0.04 inch. The needle 12 is sized to fit within the lumen of outer sleeve 30 in conventional fashion for such devices.

Figure 6:
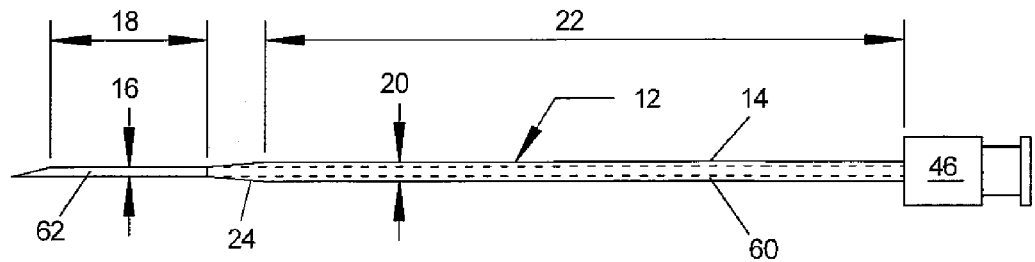
FIG. 6 presents a side view of an introducer apparatus according to another aspect of the invention.

The needle 12 may have a needle lumen (not shown) having a lancet beveled tip. Other than the first taper 24 and the change in diameters, needle 12 is a conventional small gauge needle, and may include a stainless steel shaft. The first outer diameter 16, second outside diameter 20, and first taper 24, may be formed by grinding, for example, including centerless grinding, although it is not intended to limit the invention to any specific manufacturing process. Referring now to FIG. 6, the needle 12 may be formed from a conventional needle 62 of constant diameter with a hard plastic bonded to it that forms the taper 24 and the second diameter 20 extending over the second length 22, by molding for example. In the latter example, the plastic forms a sheath 60 extending over the second length, as shown in FIG. 6.

The third outer diameter 34 may be equal to the second outer diameter 20, although the third outer diameter 34 is typically slightly larger than the second outer diameter 20. The second outer diameter 20 may be sized for a close fit with the diameter of the inner lumen 36. The first outer diameter 16 may conveniently correspond to a needle size, for example a 22 gauge needle, and the second outer diameter 20 may also conveniently correspond to a needle size, for example an 18 gauge needle.

The first taper 24 may be on the order of 2.5 to 5 mm long to allow dilation of the skin and tissue from the first diameter 16 to the second diameter 20. The second taper 38 may be on the order of 2.5 to 5 mm from the proximal end of 24 as shown in FIG. 3. The second taper 38 may be in close proximity to the first taper 24.

Figure 4:
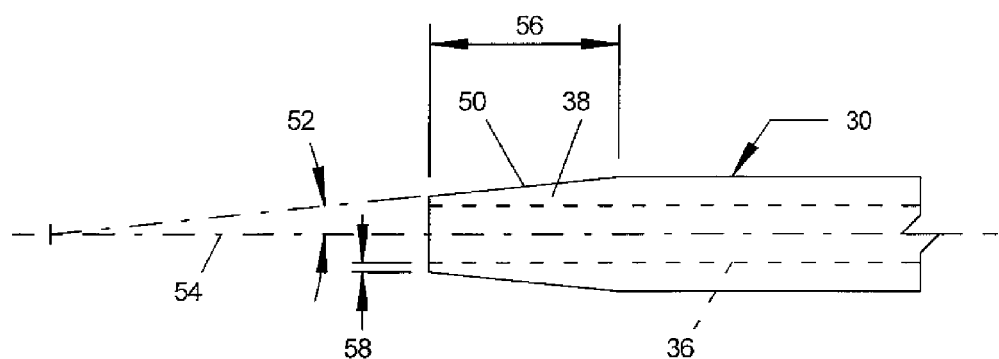
FIG. 4 is an enlarged view of the distal end of the outer sheath with parts broken away, the portion corresponding to the structure encircled by 4-4 of FIG. 2.

As best shown in FIG. 4, the second taper 38 defines an outer surface 50 that may form an acute angle 52 not exceeding on the order of 5° relative to the longitudinal axis 54 of the outer sleeve 30. The acute angle 52 may be between on the order of 0.5° and 2° relative to the longitudinal axis 54 of the outer sleeve 30. The acute angle 52 may be on the order of 1° relative to the longitudinal axis 54 of the outer sleeve 30. A lesser acute angle 52 is desirable because it tends to decrease insertion force, but this should be balanced with manufacturability.

The second taper 38 may have a longitudinal length 56 between on the order of 5 and 50 mm. The longitudinal length 56 of may be between on the order of 5 and 50 mm. The longitudinal length 56 may be between on the order of 8 and 20 mm. The longitudinal length 56 may be on the order of 15 mm. As stated, the longitudinal lengths 56 provided hereinabove may be used with outer sleeves 30 of similar French sizes (outer diameter 40), for example 5 French. For a smaller French size, such as 4 French, the longitudinal length 56 will normally be correspondingly smaller, such as on the order of 8 mm. For a larger French size, such as 6 French, the longitudinal length 56 will normally be correspondingly larger, such as on the order of 17 mm. The fourth outer diameter 40 typically is between on the order of 4 and 6 French, inclusive.

The distal end 32 may have a wall thickness 58 of between on the order of 0.0005 and 0.003 inch. The wall thickness 58 may be between on the order of 0.0005 and 0.0015 inch. The wall thickness 58 may be on the order of on the order of 0.001 inch. A typical tolerance of ∀ 0.0005 inch applies to these dimensions. A lesser wall thickness 58 is desirable because it tends to decrease insertion force, but this should be balanced with manufacturability. The teachings of US 2006/0270988 A1 are hereby fully incorporated by reference as if set forth herein.

Determining the location of the apparatus 10 from outside the body may be desirable, and the apparatus 10 may have a marker for that purpose. The marker may be visible under ultrasound and/or x-ray. The outer sleeve 30 may have a portion visible under x-ray and/or ultrasound. The outer sleeve 30 may be formed from a radiopaque material, for example a polymer loaded with a radiopaque material such as barium sulfate or tungsten, and the distal tip is visible under x-ray as the location where the outer sleeve 30 ends. Only the distal dip portion of the outer sleeve 30 may be formed from a radiopaque material, for example a polymer loaded with a radiopaque material such as barium sulfate or tungsten, with the balance formed from a radiolucent material, for example an unloaded polymer. A radiopaque band may be placed on the outer sleeve 30 proximate the distal tip. The needle 12 may also be rendered visible under ultrasound and/or x-ray. For example, the first taper 24 may be etched or dimpled to make it visible under ultrasound. The first taper 24 may also be rendered radiopaque, for example by coating it with a radiopaque material.

Figure 7:
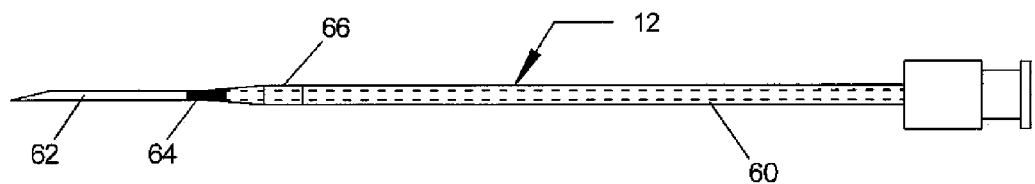
FIG. 7 presents a side view of an introducer apparatus according to another aspect of the invention.

Referring now to FIG. 7, a portion 64 of the conventional needle 62 may etched or dimpled to make it visible under ultrasound. The portion 64 may also be rendered radiopaque, for example by coating it with a radiopaque material or placing a radiopaque band on it. A radiopaque band 66 may be placed on the sheath 60 proximate the distal end of the sheath 60.

Figure 8:
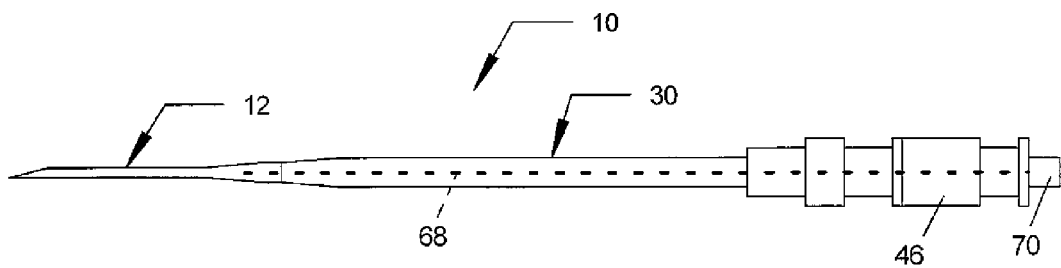
FIG. 8 presents a side view of an introducer apparatus according to another aspect of the invention.

Referring now to FIG. 8, the needle 12 may have a needle lumen and a radiopaque wire 68, gold or platinum for example, may be inserted into the needle lumen. The end of the radiopaque wire ends at a known location relative to the needle 12 and can be seen under x-ray. The proximal end of the radiopaque wire 68 may be attached to a hub 70 that butts against the hub 46. Each of the markers described above generates a visible position on the assembly 10 that allows the position of the assembly 10 to be known relative to anatomy, and each may be used alone or in combination with others.

Figure 5:
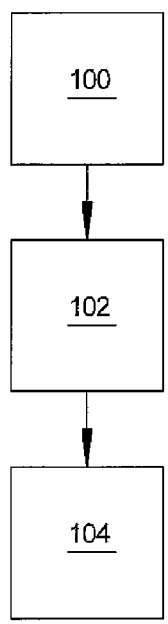
FIG. 5 presents a method according to an aspect of the invention.

According to a further aspect of the invention, a method is provided for gaining percutaneous access to a body lumen. Referring now to FIG. 5, the method comprises inserting the apparatus 10 into a body lumen, as indicated at 100, the apparatus 10 comprising: the needle 12 defining the outer surface 14 having the first outer diameter 16 along the distal first length 18, the second outer diameter 20 along the proximal second length 22, and the first taper 24 contiguous with the first outer diameter 16 and the second outer diameter 20 intermediate the first length 18 and the second length 22, the second outer diameter 20 being greater than the first outer diameter 16; and the outer sleeve 30 terminating at the distal end 32 having the third outer diameter 34 and comprising the outer sleeve lumen 36 extending longitudinally therethrough, the second taper 38 from the third outer diameter 34 at the distal end 32 to the fourth outer diameter 40 greater than the third outer diameter 34, and the shaft portion 42 having the fourth outer diameter 40 along the shaft length 44 contiguous with the second taper 38, the needle 12 being receivable within the outer sleeve lumen 36 with the second taper 38 disposed proximal of the first taper 24.

According to a further embodiment, the method may comprise withdrawing the needle 12 from within the outer sleeve 30 and leaving the outer sleeve 30 within the body lumen, as indicated at 102. The method may also comprise inserting a wire guide into the body lumen through the outer sleeve 30, as indicated at 104. The method may also comprise withdrawing the outer sleeve 30 from the body lumen leaving the wire guide in the body lumen.

In a certain embodiment, the method comprises the following steps:
1. Initial needle stick into the body lumen with the needle 12 and outer sleeve 30 in tandem.
2. Remove the needle 12 from the outer sleeve 30 leaving the outer sleeve 30 within the body lumen.
3. Insert a wire guide through the outer sleeve 30 into the body lumen.

Comparing this process to the device of the '472 patent described above in the Background section reveals that the invention eliminates three steps from the prior art method, which is quite desirable.

The apparatus 10 may be used to access larger vessels, for example the femoral artery. It delivers the outer sheath 30 into the vessel at the same time as the insertion of needle 12. According to one method, the initial needle stick collapses the proximal vessel wall all the way or close to the distal vessel wall. The needle 12 and outer sheath 30 may be pushed so that they puncture both walls. The end 32 of the outer sheath 30 may be driven into the distal vessel wall. The needle 12 may then be pulled back and withdrawn from the outer sheath 30. The outer sheath 30 may then be pulled back which will reopen the vessel lumen. Blood flushes out of the proximal end of the outer sheath 30 as soon as the distal end 32 re-enters the bloodstream. The outer sheath 30 may provide greater control on pullback because it is not as slippery as the needle 12. The sheath 30 may then be pushed further into the vessel lumen. A wire guide may then be inserted through the outer sheath 30 into the body vessel, and the outer sheath 30 may then be withdrawn. Larger dilators may then follow.

According to another method, the needle 12 is inserted at a low angle relative to the body in order to penetrate the skin and proximal vessel wall in order to gain initial access to the blood vessel. The outer sheath 30 is then pushed forward into the vessel while holding the needle 12 stationary. This prevents the needle 12 from penetrating the distal vessel wall, which may be undesirable in some instances.

The apparatus 10 may be particularly useful for gaining initial access to a body lumen.

A longer version of the apparatus 10 may also be used to perform a Neff-type procedure of the type described in the Background Section. The first step in using the set is to penetrate the skin and body with the assembly 10 and place the tip of the needle 12 at a desired location. Next, the needle 12 is removed leaving the outer sleeve 30 in place.

In summary, the apparatus 10 used in a Neff-type procedure is used according to the following steps:
1. Initial needle stick and placement of the apparatus 10.
2. Remove the needle 12 leaving the outer sleeve 30 in place.

Comparing this process to the Neff process described above in the Background section reveals that the invention eliminates three steps from the prior art method, which is quite desirable.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. An apparatus for gaining percutaneous access to a body lumen, comprising: a needle, said needle having a distal tip suitable for initial percutaneous puncture into said body lumen, said needle defining an outer surface having a first outer diameter along a distal first length, a second outer diameter along a proximal second length, and a first taper contiguous with said first outer diameter and said second outer diameter intermediate said first length and said second length, said second outer diameter being greater than said first outer diameter; and an outer sleeve terminating at a distal end having a third outer diameter and comprising an outer sleeve lumen extending longitudinally therethrough, a second taper from said third outer diameter at said distal end to a fourth outer diameter greater than said third outer diameter and proximal thereto, and a shaft portion having said fourth outer diameter along a shaft length contiguous with said second taper, said needle being receivable within said outer sleeve lumen with said second taper disposed proximal of said first taper.

2. The apparatus of claim 1, said needle and said outer sleeve comprising a positioning structure that fixes said needle to said outer sleeve.

3. The apparatus of claim 1, said needle comprising a marker visible under ultrasound.

4. The apparatus of claim 1, said needle comprising a marker visible under x-ray.

5. The apparatus of claim 1, said outer sleeve comprising a marker visible under ultrasound.

6. The apparatus of claim 1, said outer sleeve being radiopaque.

7. The apparatus of claim 1, said outer sleeve having a radiopaque distal tip.

8. The apparatus of claim 1, said needle having a needle lumen longitudinally therethrough, and comprising a radiopaque wire inserted into said lumen.

9. The apparatus of claim 1, said second taper being in close proximity to said first taper.

10. The apparatus of claim 1, said second taper having a longitudinal length between on the order of 5 and 50 mm.

11. The apparatus of claim 1, said second taper defining an outer surface at an acute angle not exceeding on the order of 5° relative to the longitudinal axis of the outer sleeve.

12. The apparatus of claim 1, said second taper defining an outer surface at an acute angle between on the order of 0.5° and 2° relative to the longitudinal axis of the outer sleeve.

13. The apparatus of claim 1, said second taper defining an outer surface at an acute angle on the order of 1° relative to the longitudinal axis of the outer sleeve.

14. The apparatus of claim 1, said distal end having a wall thickness of between on the order 0.0005 and 0.003 inch.

15. A method for gaining percutaneous access to body anatomy, comprising: providing an apparatus for insertion into body anatomy, said apparatus comprising: a needle having a distal tip suitable for initial percutaneous puncture into said body anatomy, said needle having a first outer diameter along a distal first length and a tip at a distal end of said first length suitable for said insertion, a second outer diameter along a proximal second length, and a first taper contiguous with said first outer diameter and said second outer diameter intermediate said first length and said second length, said second outer diameter being greater than said first outer diameter; and an outer sleeve terminating at a distal end having a third outer diameter and comprising an outer sleeve lumen extending longitudinally therethrough, a second taper from said third outer diameter at said distal end to a fourth outer diameter greater than said third outer diameter and proximal thereto, and a shaft portion having said fourth outer diameter along a shaft length contiguous with said second taper, said needle being receivable within said outer sleeve lumen with said second taper disposed proximal of said first taper; and inserting said apparatus into said body anatomy.

16. The method of claim 15, said body anatomy being a body lumen.

17. The method of claim 15, said body anatomy being an organ.

18. The method of claim 15, comprising withdrawing said needle from within said outer sleeve and leaving said outer sleeve within said body anatomy.

19. The method of claim 15, comprising withdrawing said needle from within said outer sleeve and leaving said outer sleeve within said body anatomy, and inserting a wire guide into said body lumen through said outer sleeve.

20. The method of claim 15, comprising withdrawing said needle from within said outer sleeve and leaving said outer sleeve within said body anatomy, inserting a wire guide into said body anatomy through said outer sleeve, and withdrawing said outer sleeve from said body anatomy leaving said wire guide in said body anatomy.

21. The apparatus of claim 1, wherein said needle has a lancet beveled tip.

* * * * *